(12) United States Patent
Peled et al.

(10) Patent No.: US 11,413,089 B2
(45) Date of Patent: *Aug. 16, 2022

(54) ABLATION TECHNIQUES FOR THE TREATMENT OF ATRIAL FIBRILLATION

(71) Applicant: CardioFocus, Inc., Marlborough, MA (US)

(72) Inventors: Omer Peled, Haifa (IL); Anthony Jason Mirabito, Derry, NH (US)

(73) Assignee: CardioFocus, Inc., Marlborough, MA (US)

( * ) Notice: Subject to any disclaimer, the term of this patent is extended or adjusted under 35 U.S.C. 154(b) by 223 days.

This patent is subject to a terminal disclaimer.

(21) Appl. No.: 16/578,295

(22) Filed: Sep. 21, 2019

(65) Prior Publication Data

US 2020/0113626 A1 Apr. 16, 2020

Related U.S. Application Data

(60) Continuation of application No. 14/970,799, filed on Dec. 16, 2015, now Pat. No. 10,517,669, which is a continuation of application No. 14/658,214, filed on Mar. 15, 2015, now abandoned, which is a division of application No. 13/772,472, filed on Feb. 21, 2013, now Pat. No. 8,992,514.

(60) Provisional application No. 61/602,653, filed on Feb. 24, 2012.

(51) Int. Cl.
*A61B 18/12* (2006.01)
*A61B 18/14* (2006.01)
(Continued)

(52) U.S. Cl.
CPC .......... *A61B 18/1492* (2013.01); *A61B 18/02* (2013.01); *A61B 18/20* (2013.01); *A61B 18/24* (2013.01); *A61B 5/0538* (2013.01); *A61B 2018/0016* (2013.01); *A61B 2018/0022* (2013.01); *A61B 2018/00166* (2013.01); *A61B 2018/00351* (2013.01); *A61B 2018/00357* (2013.01); *A61B 2018/00375* (2013.01); *A61B 2018/00577* (2013.01); *A61B 2018/00875* (2013.01); *A61B 2018/0212* (2013.01); *A61B 2018/0262* (2013.01); *A61B 2018/2244* (2013.01); *A61B 2018/2272* (2013.01); *A61F 2007/126* (2013.01)

(58) Field of Classification Search
CPC ..... A61B 18/1492; A61B 18/20; A61B 18/24; A61B 2018/0022; A61B 2018/0351; A61B 2018/00577; A61B 2018/2244
See application file for complete search history.

(56) References Cited

U.S. PATENT DOCUMENTS 6,405,732 B1 6/2002 Edwards et al.
6,427,089 B1 7/2002 Knowlton
(Continued)

FOREIGN PATENT DOCUMENTS

WO 2005112812 12/2005

OTHER PUBLICATIONS

European Search Report, Corresponding EP Application No. 13751219, dated Nov. 16, 2015, 6 pages.

*Primary Examiner* — Daniel W Fowler
(74) *Attorney, Agent, or Firm* — Leason Ellis LLP

(57) ABSTRACT

A catheter device provides a balloon structure and a side-firing laser lumen within the balloon to create lesions in the pulmonary vein (PV) in the treatment of atrial fibrillation. Mounted on the balloon so as to contact the PV when the balloon is inflated are one or more electrodes which may be used in a measurement mode, a treatment mode, or both.

6 Claims, 6 Drawing Sheets

(51) Int. Cl.
*A61B 18/24* (2006.01)
*A61B 18/02* (2006.01)
*A61B 18/20* (2006.01)
A61B 18/22 (2006.01)
A61B 18/00 (2006.01)
A61B 5/0538 (2021.01)
A61F 7/12 (2006.01)

(56) References Cited

U.S. PATENT DOCUMENTS

| | | |
|---|---|---|
| 7,137,395 B2 | 11/2006 | Fried et al. |
| 7,399,300 B2 | 7/2008 | Bertolero et al. |
| 7,492,987 B2 | 2/2009 | Yeik et al. |
| 8,337,492 B2 | 12/2012 | Kunis et al. |
| 2001/0007940 A1 | 7/2001 | Tu |
| 2002/0082610 A1 | 6/2002 | Cloanta et al. |
| 2002/0198521 A1 | 12/2002 | Maguire |
| 2003/0028183 A1 | 2/2003 | Sanchez |
| 2003/0093072 A1 | 5/2003 | Friedman |
| 2003/0120270 A1 | 6/2003 | Acker |
| 2004/0158237 A1 | 8/2004 | Abboud |
| 2005/0059965 A1 | 3/2005 | Eberl et al. |
| 2005/0251116 A1 | 11/2005 | Steinke et al. |
| 2006/0015162 A1 | 1/2006 | Edward et al. |
| 2006/0069385 A1 | 3/2006 | Lafontaine |
| 2006/0106375 A1 | 5/2006 | Werneth et al. |
| 2007/0083194 A1 | 4/2007 | Kunis et al. |
| 2007/0282403 A1 | 12/2007 | Tearney et al. |
| 2009/0131930 A1 | 5/2009 | Gelbart |
| 2009/0299355 A1 | 12/2009 | Bencini |
| 2010/0076299 A1 | 3/2010 | Gustus |
| 2010/0204560 A1 | 6/2010 | Salahieh |
| 2010/0249568 A1 | 9/2010 | Stehr |
| 2012/0035601 A1 | 2/2012 | Wittenberger |

ABLATION TECHNIQUES FOR THE TREATMENT OF ATRIAL FIBRILLATION

RELATED APPLICATIONS

This application is a continuation application of U.S. Ser. No. 14/970,799, filed Dec. 16, 2015, which is a continuation application of U.S. Ser. No. 14/658,214, filed Mar. 15, 2015, now abandoned, which is a divisional application of U.S. Ser. No. 13/772,472, filed Feb. 21, 2013, now U.S. Pat. No. 8,992,514, granted on Mar. 31, 2015, which claims priority to Ser. No. 61/602,653, filed Feb. 24, 2012, the disclosures of which are incorporated herein by reference in their entirety.

FIELD OF THE INVENTION

This invention relates to improvements in the field of atrial fibrillation, including devices and methods for the treatment of atrial fibrillation using new and improved apparatus.

BACKGROUND OF THE INVENTION

Pulmonary vein ablation is a known surgical treatment for atrial fibrillation (AF). Current solutions are based on a single energy source e.g. RF, cryogenic, ultrasound, laser or microwave. Each modality has its own advantages and disadvantages both in terms of tissue interaction or delivery method.

In order to optimize the treatment, a uniform transmural lesion must be created in the target tissue. Overtreatment may result in irreversible collateral thermal or mechanical damage to surrounding tissue which may lead to perforation or other complications while insufficient lesion creation may not electrically isolate the PV from the left atrium wall. With some of the technologies available today, due to the nature of the treatment modality, it is difficult to determine at what point the treatment desired is sufficiently administered.

For example, in a known treatment technique using a cryogenic fluid, the fluid is introduced into a balloon catheter which may be positioned within the pulmonary vein (PV). From experience and prior knowledge the operating doctor may have determined the length of time the fluid should be in contact with the tissue to achieve the desired ablation and creation of a lesion in the tissue. However, this may be imprecise and can vary from doctor to doctor and with the patient's tissue makeup. Further, introduction of the cryogenic fluid, its withdrawal, and stopping the creation of the lesion is imprecise given that the cooling of the tissue is gradual and to some extent not precisely controllable. Thus, there remains a need to provide an ablation system that permits more precise control of the creation of a lesion and for controllably halting the extent of the damage created by the lesion.

Another example is the creation of a lesion using radio frequency (RF) energy.

Typically, unlike a cryogenic solution, in the treatment of AF using a RF source, a balloon is not used, but rather a catheter with one or more electrodes is introduced into the PV and the electrodes activated. Again, as in the example of the cryogenic treatment, the duration of treatment and the extent of damage caused by the application of RF may be imprecise and only loosely controllable. Thus, there is a need to provide a RF ablation system that permits more precise control and monitoring of a lesion created by the application of RF energy.

SUMMARY OF THE INVENTION

One aspect of the invention in the present application is to create a system which combines different modalities in a unique structure. Based on its nature, some modalities can be used for treatment or for measuring and diagnostic purposes in order to monitor the lesion dimension and quality and to feedback the system in order to optimize the treatment.

The present invention provides a device suitable for insertion into the pulmonary vein for the treatment of atrial fibrillation and in particular may include at least one aperture lumen having distal and proximal ends as well as an inflatable balloon in the vicinity of the distal end of the lumen. An optical fiber may be positioned at least partially within the at least one lumen; and there may be at least one opening in the vicinity of the distal end and within the inflatable balloon. An optical device may be placed in the lumen in the vicinity of the distal end and within the balloon to deflect a laser beam introduced in the vicinity of the proximal end and exiting in the vicinity of the distal end of the lumen. At least one electrode may be formed on the balloon, and the at least one electrode may be suitable for one or both of measurement and treatment of the pulmonary vein. A controller may be operatively connected to the at least one electrode, such that, when the inflatable balloon is inflated, the at least one electrode comes into contact with the pulmonary vein wall for one or more of measurement and treatment of atrial fibrillation.

BRIEF DESCRIPTION OF THE DRAWINGS

In the drawings, in which like reference numerals indicate related parts are elements of the embodiments of the present invention throughout the several views.

DETAILED DESCRIPTION OF THE PREFERRED EMBODIMENTS

RF is presently the dominant technology for PV ablation and, as mentioned, does not require a balloon at all. RF is delivered directly to the target tissue by coil electrodes, in a variety of shapes, and delivered through a catheter.

Known laser ablation systems deliver the laser energy through a side firing fiber located in a fixation balloon. Laser ablation systems have the advantage that the interaction of tissue to various types and wavelengths of laser beams is well-known in the art, in terms of absorption of the heat generated by the beam and the extent and timing of cooling of the irradiated tissue. In addition, the use of laser beams to ablate tissue has the advantage that the beam can be instantly turned on and off, allowing a more precise control of the creation of a lesion and ablation than with either the cryogenic or RF modalities. The beam may be delivered from the inner volume of a balloon, through its wall, to the target tissue. The beam may exit the balloon along a strip which acts as a window. The optical window in the balloon material is, of course, chosen so as to be transparent to the laser beam so that balloon integrity is maintained during ablation. An example of a laser treatment system suitable for the treatment of AF but without measuring features or functionality is given in U.S. Pat. No. 7,137,395 entitled "Circumferential Pulmonary Vein Ablation Using a Fiberoptic Balloon Catheter", the entire disclosure of which is herein incorporated by reference in its entirety. One aspect of the present invention is to create a balloon which has at least one, but perhaps more than one, measuring element on either side of the area of the balloon through which the laser beam passes, called herein the treatment strip. In one configuration, two or more arrays of such elements can be positioned from both sides of the laser treatment strip. Each array may have one or more rows of elements.

Each measuring element may be an RF electrode or an Ultrasound transducer, and is embedded on the outer surface of the balloon's wall and is wired with flexible wires also embedded on or in the balloon. Each element has an outer surface which is configured to create a direct contact with the tissue when the balloon is inflated.

Figure 1:
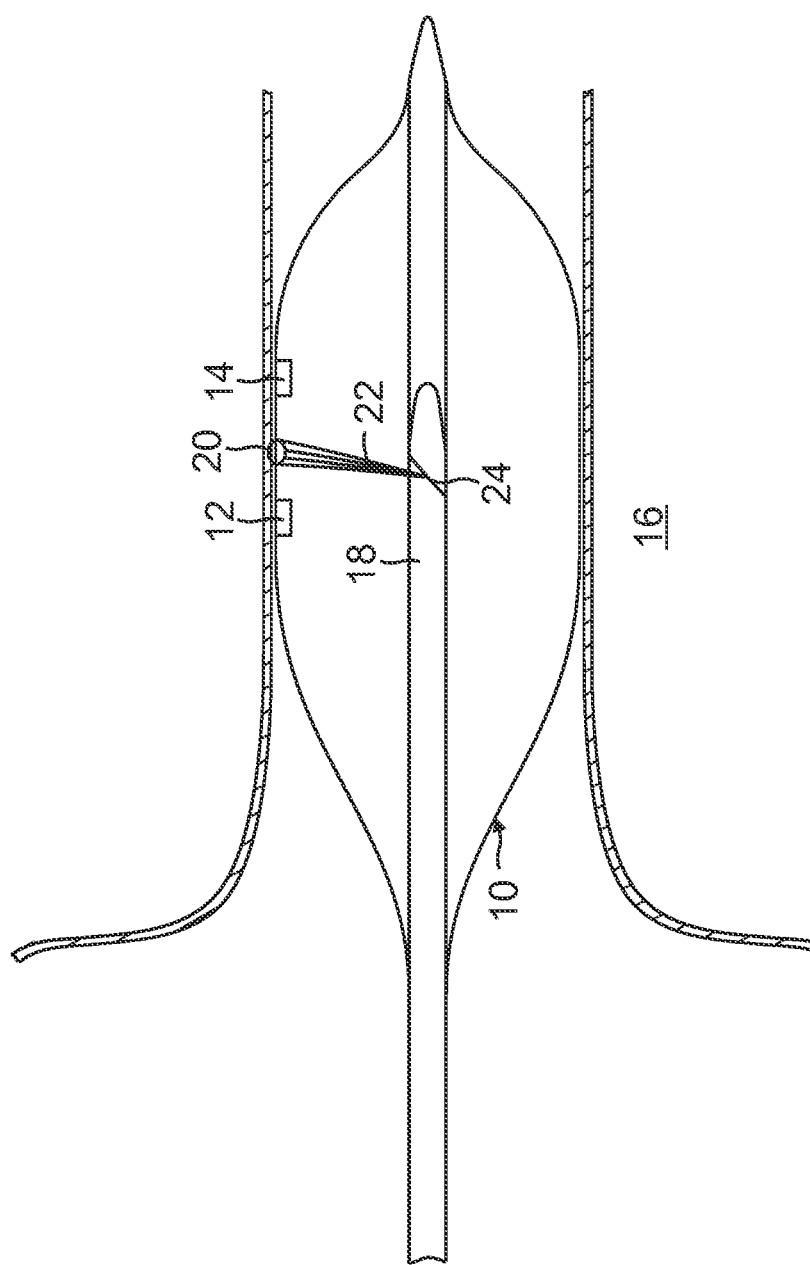
FIG. 1 is a diagram of a laser ablation balloon device in accordance with the present invention.

Turning now to the Figures, FIG. 1 shows one aspect of the invention in which a balloon 10 with measuring elements 12 and 14 is positioned within the PV 16. A side firing fiber 18 located in the balloon targets a tissue region 20 within a treatment strip through the balloon. As illustrated in FIG. 1, a surface 24 is used to deflect the beam spot from along the length axis of the catheter to an angle to impact the surface of the PV. While FIG. 1 shows this to be approximately 90 degrees, it is to be understood that any suitable angle may be utilized. One structure to deflect the beam may be to angle the face of the firing fiber to totally internally reflect the beam out of the face of the fiber in a direction transverse to the length axis of the catheter, although any suitable desired angle may be chosen, as disclosed in U.S. Pat. No. 5,772,657, entitled "Side Firing Fiber Optic Laser probe", the entirety of which is herein incorporated by reference. An angled mirror facing the exit of the laser fiber may be utilized to deflect the beam. The beam spot 22 can manually or automatically scan (by rotation) the treatment strip to ablate the PV wall. Measuring elements 12 and 14 from both sides of the strip can also treat tissue located between active pair of elements. It is known in the art that electrodes of the radio-frequency type and the ultrasonic type can be used alternatively in a measuring mode or a treatment mode, thus enabling the ablation device of the present invention to both measure the degree of success of ablation as well as to operate in conjunction with the side firing laser to provide treatment to the PV. Bipolar RF electrodes can be activated by a system controller (not shown) in a variety of sequences (measuring and/or treatment) to generate treatment and/or measuring vectors. In one example, illustrated in FIG. 4, the vectors 30 can crisscross each other and generate multiple adjacent X shapes from RF electrodes 32 (A1-A7, B1-B7) in addition to the laser treatment. In yet another embodiment, the multiple electrodes 32 can measure tissue impedance changes resulting from the laser treatment or any other treatment and to assess the size, depth or electrical quality of a lesion. This information can be fed back to the system controller for further treatment.

Figure 3:
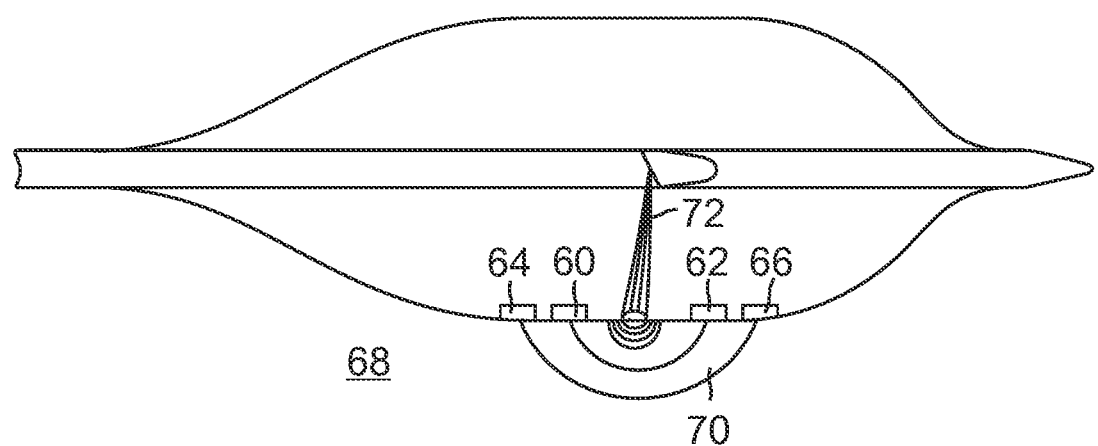
FIG. 3 is an alternative embodiment to that of FIG. 1 which includes a number of treatment electrodes.
Figure 4:
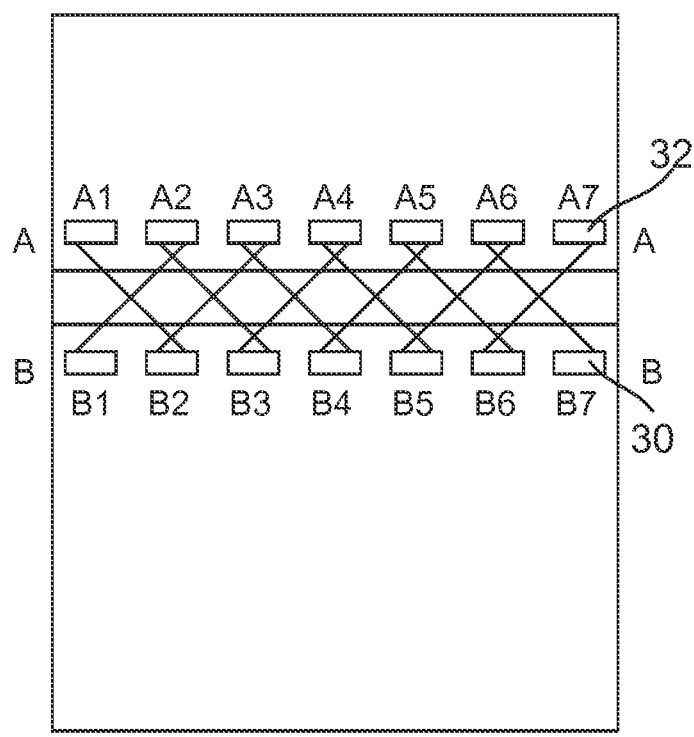
FIG. 4 is a variation of the embodiment of FIG. 3 and includes a number of cross related RF electrodes.

In yet in another configuration, the RF electrodes 32 may be replaced by ultrasound transducers which in the embodiments if FIGS. 1, 3 and 4 may measure changes in the mechanical properties of the tissue by measuring changes of sound velocity, absorption or reflection in different energies or frequencies of the target tissue. Multiple elements can be used to focus ultrasound energy in order to also achieve therapeutic threshold and to ablate tissue ultrasonically rather than use RF energy.

Figure 2:
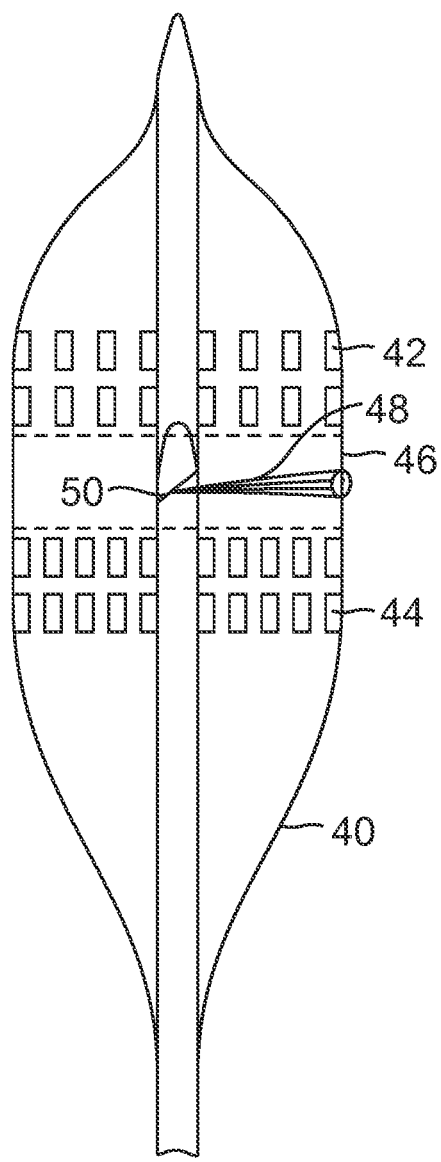
FIG. 2 is another embodiment of the invention of FIG. 1 in which there are a plurality of arrays of measuring elements.

Turning now to FIG. 2. FIG. 2 shows the side firing balloon catheter 40 including a laser ablation strip 46 through which laser energy is focused upon the PV. In the embodiment shown in FIG. 2, two rows of measuring and/or treating elements 42 and 44 are positioned on either side of the laser ablation strip 46 in order to measure and/or treat the PV in conjunction with or in lieu of the laser beam 48 from the side firing laser 50.

In addition to measuring changes in the tissue, the ultrasound elements may be used for measuring, for example, the thickness of the PV wall, which may aid the operating doctor to determine the extent of treatment applied to the tissue. The ultrasound elements may be used to measure the overall dimensions of not only the PV but also the dimensions of the lesion(s) created by the treatment.

In another configuration illustrated in FIG. 3, the RF electrode array may include more than one row of electrodes in each side of the treatment strip. As shown in FIG. 3, the inner pair 60, 62 can create an electric field which then pushes the electric field 70 created by pair 64, 66 deeper into the target tissue 68. A third pair (not illustrated) may be used to push the electric field even deeper. More pairs can be utilized in order to fully cover the PV wall. A pair of the RF electrodes, for example, can be configured to deliver energy fluence to ablate a tissue in a certain depth in conjunction with the laser ablation beam 72 or in lieu of such beam or alternatively between energization of the laser ablation beam 72 and RF electrodes 60, 62, 64 and 66. The same pair of electrodes can then be configured to deliver non-ablative energy and to only push deeper the ablative energy of the next pair. Using this sequence of events can create a homogenous lesion across the PV wall to achieve the best electrical isolation safely.

Figure 5:
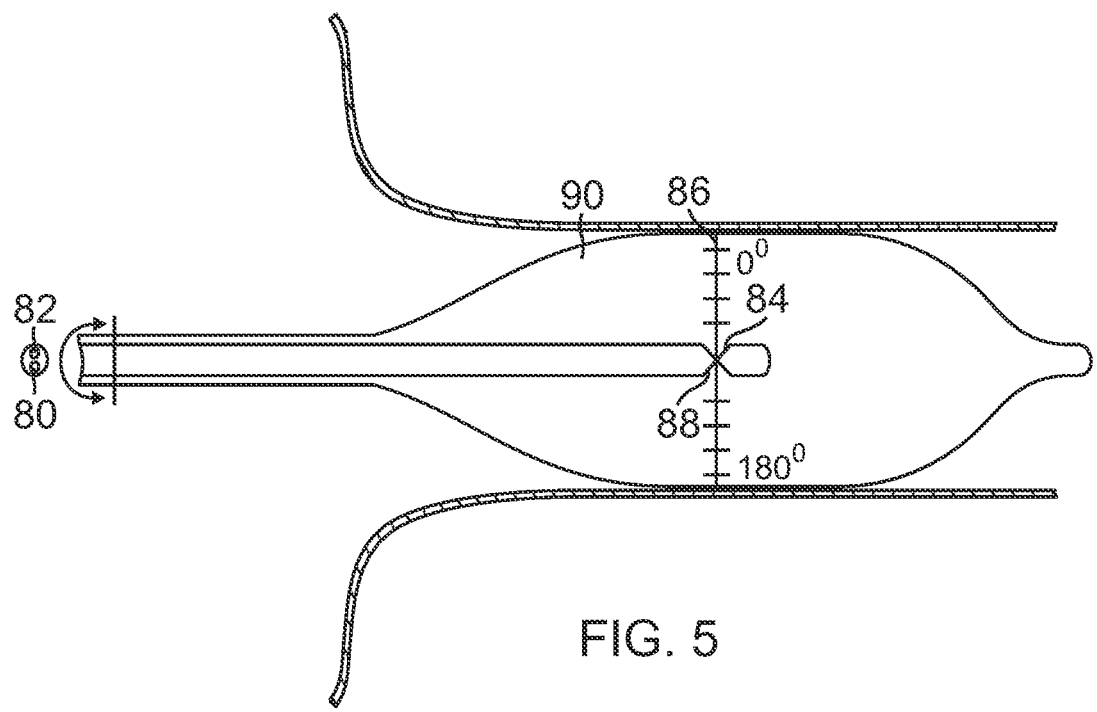
FIG. 5 is an alternative embodiment of FIG. 1 and includes 2 lumens, a laser lumen and a viewing lumen.
Figure 5A:
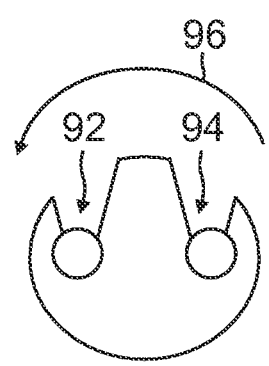
FIG. 5A is an alternative embodiment of FIG. 5 including a laser lumen and a viewing lumen.
Figure 6:
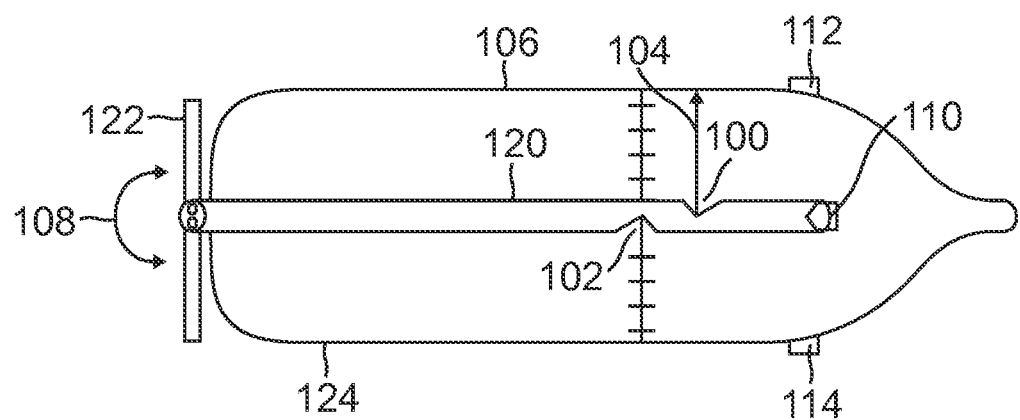
FIG. 6 is an embodiment related to FIG. 5 illustrating the ability of the laser viewing lumens to rotate about an axis within the balloon.

Turning now to FIG. 5, this figure is similar to that shown in FIG. 1 but includes a second fiber viewing lumen 80 arranged in parallel "over-under" relationship to the side firing fiber lumen 82 for the laser beam. In this embodiment, the second side-viewing fiber lumen 80 is incorporated that views the inside of the balloon with an 180 degree offset from that of the side-firing fiber 82 lumen (as shown, although other angular offsets may be utilized). However, one way to visualize the extent of lesion creation immediately after the laser firing is to orient the firing and viewing lumens "side-by-side" rather than in the "over-under" relationship of FIG. 5. This is illustrated in FIG. 5A, in which the lumens 92 and 94 sit side-by-side, the firing laser lumen being 92 and the viewing lumen being 94. When the lumen 92, 94 combination is rotated in direction 96, the laser fires through lumen 92 and the results are viewable through lumen 94. Of course, lumens 92 and 94 may be "in line" with one another, as shown in FIG. 5 or "offset" from one another, as shown in FIG. 6, to be discussed below. However, any suitable angle or orientation between the firing and viewing lumens may be utilized.

For both of FIGS. 5 and 5A, it is to be understood that with both the side-firing lumens and the side-viewing lumens that the light beams are reoriented from along the lumens axis to an angle from such axis using any number of devices described above with respect to the embodiment of FIG. 1. As shown in FIG. 5, the second side-viewing fiber lumen 80 includes an opening 88 in the lumen 80 which allows the light from the viewing fiber to be angled from a position along the longitudinal axis length of the lumen to one at an angle with respect to the lumen longitudinal axis. While the operating doctor may wish to move the side firing laser 84 around the periphery of the balloon in a circular motion while firing the laser, there are at least two visualization problems. The first is knowing where the laser is in fact firing and whether areas of the PV sought to be treated are either not treated or treated too much. The second is that while the operating doctor may rotate the proximal end of the side-firing 84 fiber a given number of degrees, due to torsional forces within the fiber itself, the same given degrees of rotation may not translate precisely with the working distal end of the side-firing fiber 84, again potentially providing either over or under treatment. While the viewing lumen may be of a conventional type, instead an optical coherence tomography (OCT) device may be incorporated in the viewing lumen as well or instead of the conventional type.

Thus, we have provided, in addition to the second viewing fiber lumen 80, a series of markings 86, shown as lines in FIG. 5 for illustration only, either on the inside or the outside of the balloon 90, that may be viewed through the viewing fiber, again accounting for the 180 (or other) degree offset. Thus, the operating doctor will not only be able to view the extent of the lesion made by the use of the laser energy but will also know the precise position of the side-firing fiber and the areas of the lesion within the PV that require further (or less) ablation. The markings may be marked from 0 degrees to 360 degrees or with any other suitable scale. In addition, as shown in FIG. 6, the side-firing laser fiber 100 opening and the viewing fiber 102 opening may be offset from one another so that the markings do not interfere with the window within which the laser beam 104 operates. The combined side-firing and viewing fibers may be rotated in either direction, as illustrated by arrow 108.

In addition, due to the extent of miniaturization of electronic elements, it may be useful to incorporate positioning determining elements within the balloon itself. One possible technology is MediGuide's (now St. Jude Medical) MPS imagery technology on the distal end of the side-firing fiber to give the operating doctor a 3D perspective of the balloon position vis-à-vis the PV.

A further peripheral that may be utilized is a suitable sensor such as sensor 110 shown in FIG. 6 located at the distal tip of the side-firing fiber 120 which can interact with the circumferentially disposed RF or ultrasound electrodes 112, 114 to determine the location or orientation of the side-firing fiber tip within the balloon and relative to a treatment window or within the PV.

Yet another embodiment, illustrated in FIG. 6, to assure accurate positioning and orientation of the side-firing fiber 120 and the treatment area is to equip the fiber with an electromagnetically actuated manipulator 122 that controls rotation and/or displacement of the side-firing fiber's distal end. Suitable electrical connections may be made to a manipulation device/toggle at the proximal end of the fiber which may be manipulated by the operating doctor. While the electromagnetically manipulator 122 is shown in FIG. 6 to be located just outside the balloon 124 it is understood that it is within the scope of the invention that the actuator 122 may be located within the balloon 124. This may be combined with the direct visualization or the sensor 110 described above to give the operating doctor direct positional orientation information of the side-firing fiber.

Figure 7:
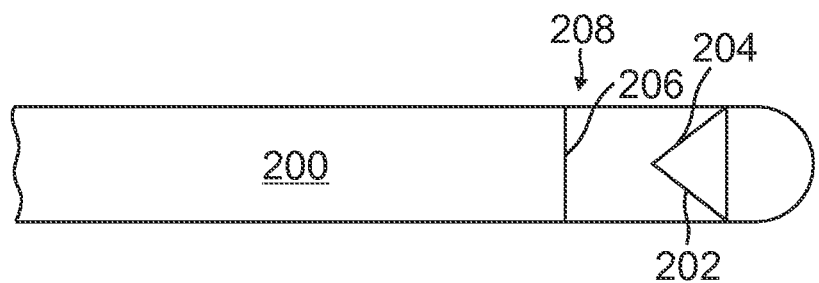
FIG. 7 is an alternative to the side firing laser of FIG. 1 and includes a conical shape reflector.

Turning now to FIG. 7, this figure illustrates another form of a laser fiber treatment device. While the lasers shown in FIGS. 1, 5 and 6 are side-firing devices, the laser fiber structure shown in FIG. 7 is a 360 degree firing laser. In lieu of the flat but angled mirror surface shown (24 in FIG. 1) in FIGS. 1, 5 and 6, at the distal end of the fiber 200 is installed a conically shaped mirror or reflector 202, with the apex 204 of the cone disposed to face 206 the laser-firing fiber 200. In this manner, when the laser beam is directed to the mirror, the beam will be reflected 90 degrees to the laser beam axis and reflected in a 360 degree circular beam. In order to accomplish this, between the distal end of the fiber and conical mirror is disposed a tube-like window 208 of a suitable material around the entire circumference of the tube containing the fiber to allow the laser beam reflected from the conical mirror to pass out of the catheter. The material chosen for the window preferably is a material transparent to the laser beam itself. While FIG. 7 illustrates a 90 degree reflection from the conically shaped mirror or reflector, it is to be understood that the cone shape or height may be chosen to reflect the laser beam at other than 90 degrees depending on the desired orientation.

Figure 8:
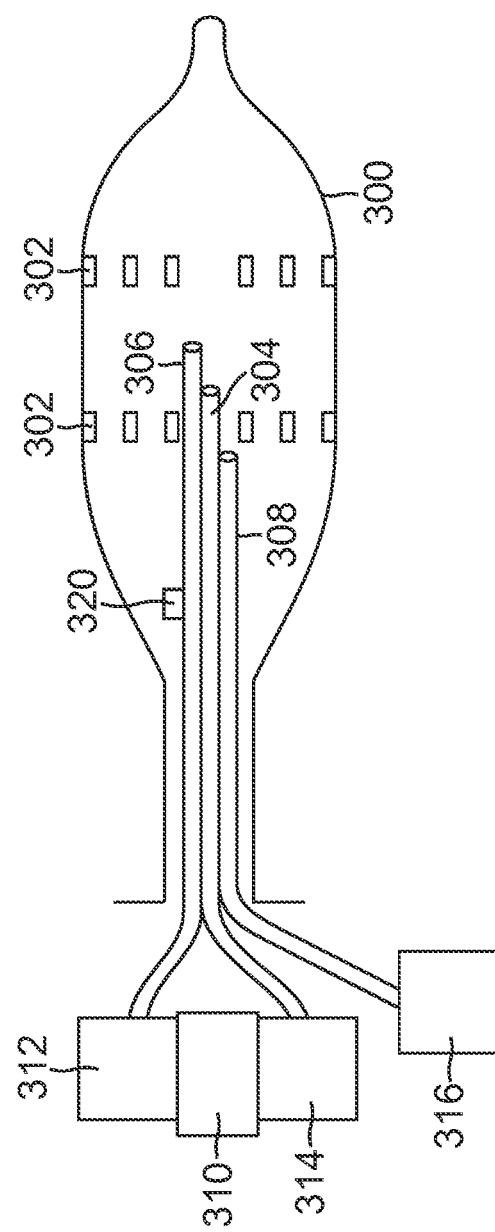
FIG. 8 is an improved cryogenic balloon device which provides heat and cooling control as well as RF sensors.

Turning now to FIG. 8, that figure illustrates improvements to a cryogenic-based ablation system. As discussed above, one problem with known cryogenic systems is the lack of precision that may result in either undertreatment or overtreatment of the PV in terms of lesion creation. In FIG. 8, to a presently-known cryogenic balloon catheter 300, such as that made by Medtronic, two improvements are added. The first is a series of RF or other (such as ultrasonic) sensors 302 of the type as previously described in connection with FIG. 2. The second is the addition of a source 312 of a heated fluid which may be introduced either through the same lumen 304 as the cold fluid is introduced or through a second lumen 306. In addition, a third lumen 308 may be provided to remove cold and/or heated fluid from the balloon and return it to the system. In operation, cold fluid from source 314 is introduced into the balloon 300 as is presently known through lumen 306. The RF or other sensors 302 are activated to assess the lesion caused in the PV by the application of cold fluid. Once the desired lesion has been created or is the process of creation, the RF sensors which are operatively connected to a system controller 310 will signal the system controller to provide heated fluid to the catheter and thus to the balloon to halt the ablation of the PV. The third lumen 308 may be utilized at this juncture to remove all the fluid within the balloon return to a volume 316 in which it may be reused or discarded. It is to be understood that the terms "Cold fluid" and "heated fluid" are used relatively herein, inasmuch as the temperatures of cold fluid being introduced are well established in cryogenic devices being marketed presently. In particular, the term "heated fluid" means fluid which is of a temperature greater than, to any degree, to that of the "cold fluid". The ability to control the introduction of both cooled and heated fluid also allows for treatments in which the tissue may be alternatively cooled and heated in order to achieve the desired treatment effect. In lieu of a heated fluid being introduced into the balloon, the second lumen 304 may be constructed of a resistive-type heating element to heat the cold fluid already present within the balloon. One or more thermocouples 320 may be provided with the balloon itself and on the balloon outside surface to determine tissue and fluid temperatures operatively connected to and in conjunction with the controller apparatus 310. It is further to be understood that only the first improvement discussed above or the second improvement discussed above may be provided on the cryogenic balloon catheter 300.

It is further to be understood that the RF or other (ultrasound) sensors may be reversed in their function and operate as further sources for causing ablation. For example, the PV may be subjected to both a cryogenic treatment followed by an RF treatment of the type discussed in connection with FIGS. 1-4 above, or vice versa, or even an alternate cryogenic/RF treatment repeated a desired number of times.

Finally, as mentioned, in a typical RF ablation device, a balloon is not utilized, but rather, typically, coils with electrodes are positioned in the PV or other desired location. Mounting RF electrodes on the outer surface of a balloon, as shown in various figures herein, allows direct and precise contact between the electrodes and tissue. In addition, in such a balloon RF ablation device, a side-viewing optical fiber of the type described with reference to FIG. 5 may be utilized to provide visual inspection of lesion created by the RF ablation coil.

The advantages of the invention described in this application have been set forth in the foregoing description and in the appended drawings. It will be understood, however, that this disclosure is, in any number of respects, only illustrative. Changes may be made in details including such matters as shape, size, arrangement of parts without departing from the scope of the present invention. The scope of the invention herein is defined by the appended claims now following.

What we claim is:

1. A method of treating a human for atrial fibrillation, the method comprising:
    providing a device suitable for insertion into the pulmonary vein for the treatment of atrial fibrillation, the device comprising: at least one apertured lumen having distal and proximal ends; an inflatable balloon in the vicinity of the distal end of the lumen; an optical fiber at least partially within the at least one lumen and disposed along the axis of the lumen, the optical fiber being suitable for conveying a beam of laser energy; at least one opening in the vicinity of the distal end and within the inflatable balloon; an optical device on the optical fiber in the vicinity of the distal end and within the balloon to deflect a laser beam introduced in the vicinity of the proximal end and exiting in the vicinity of the distal end of the lumen at angles other than along the lumen axis, wherein the deflected laser energy impinges on the pulmonary vein wall through the inflated balloon; the optical fiber being rotatable around the lumen axis while the inflatable balloon remains stationary; at least one electrode formed on the balloon, wherein the at least one electrode may be activated to one or both of measurement and treatment of the pulmonary vein wall; wherein, when the inflatable balloon is inflated, the at least one electrode comes into contact with the pulmonary vein wall;
    providing an electromagnetically actuated manipulator that is controllable to rotate the optical fiber around the lumen axis;
    providing a controller operatively connected to: (1) cause inflation of the inflatable balloon, (2) activate the at least one electrode, (3) to a source of laser energy, the source of laser energy being operable to cause laser energy to be conveyed along the lumen axis of the optical fiber to the optical device, the optical device deflecting the laser beam to impinge on the pulmonary vein wall, and (4) the manipulator to rotate the optical fiber around the lumen axis;
    wherein the method comprises the steps of the controller:
    inflating the inflatable balloon;
    controlling the source of laser energy to cause laser energy to impinge on the pulmonary vein wall;
    controlling the manipulator to rotate the optical fiber around the lumen axis while the laser energy impinges on the pulmonary vein wall; and,
    operating the at least one electrode for one of measurement before or after the laser energy has impinged on the pulmonary vein wall.

2. The method of claim 1, wherein the optical device is a surface which deflects the laser beam from along the lumen axis to the pulmonary vein wall.

3. The method of claim 2, wherein the optical device is an angled mirror.

4. The method of claim 1, wherein the at least one electrode is one or more of an electrode for applying RF or ultrasound energy to the pulmonary vein wall.

5. A method of treating a human for atrial fibrillation, the method comprising:
    providing a device suitable for insertion into the pulmonary vein for the treatment of atrial fibrillation, the device comprising: at least one apertured lumen having distal and proximal ends; an inflatable balloon in the vicinity of the distal end of the lumen; an optical fiber at least partially within the at least one lumen and disposed along the axis of the lumen, the optical fiber being suitable for conveying a beam of laser energy; at least one opening in the vicinity of the distal end and within the inflatable balloon; an optical device on the optical fiber in the vicinity of the distal end and within the balloon to deflect a laser beam introduced in the vicinity of the proximal end and exiting in the vicinity of the distal end of the lumen at angles other than along the lumen axis, wherein the deflected laser energy impinges on the pulmonary vein wall through the inflated balloon; the optical fiber being rotatable around the lumen axis while the inflatable balloon remains stationary;
    providing an electromagnetically actuated manipulator that is controllable to rotate the optical fiber around the lumen axis;
    providing a controller, the controller being operatively connected to: (1) cause inflation of the inflatable balloon, (2) to a source of laser energy, the source of laser energy being operable to cause laser energy to be conveyed along the lumen axis of the optical fiber to the optical device, the optical device deflecting the laser beam to impinge on the pulmonary vein wall, and (3) the manipulator to rotate the optical fiber around the lumen axis;
    wherein the method comprises the steps of the controller:
    inflating the inflatable balloon;
    controlling the source of laser energy to cause laser energy to impinge on the pulmonary vein wall; and,
    controlling the manipulator to rotate the optical fiber around the lumen axis while the laser energy impinges on the pulmonary vein wall.

6. The method of claim 5, wherein the optical device is a surface which deflects the laser beam from along the lumen axis to the pulmonary vein wall.

* * * * *